US00PP37120P3

(12) United States Plant Patent
Huber

(10) Patent No.: US PP37,120 P3
(45) Date of Patent: Dec. 2, 2025

(54) ***DAHLIA* PLANT NAMED 'LeeAnn'S FD61A'**

(50) Latin Name: *Dahlia hybrida*
Varietal Denomination: LeeAnn's FD61A

(71) Applicant: Coseytown Flowers llc, Greencastle, PA (US)

(72) Inventor: LeeAnn Huber, Greencastle, PA (US)

(73) Assignee: Coseytown Flowers LLC, State Line, PA (US)

( * ) Notice: Subject to any disclaimer, the term of this patent is extended or adjusted under 35 U.S.C. 154(b) by 0 days.

(21) Appl. No.: 18/999,438

(22) Filed: Dec. 23, 2024

(65) Prior Publication Data

US 2025/0261571 P1 Aug. 14, 2025

Related U.S. Application Data

(60) Provisional application No. 63/552,455, filed on Feb. 12, 2024.

(51) Int. Cl.
*A01H 5/02* (2018.01)
*A01H 6/14* (2018.01)

(52) U.S. Cl.
USPC ..... Plt./321

(58) Field of Classification Search
USPC ..... Plt./321
CPC . A01H 5/02; A01H 5/00; A01H 6/144; A01H 6/14
See application file for complete search history.

(56) References Cited

U.S. PATENT DOCUMENTS

PP18,422 P2 * 1/2008 Verwer ..... A01H 6/14 Plt./321

OTHER PUBLICATIONS

Hardy Echo-Pilot New *dahlia* name is a tribute to two Greencastle Dollys 2022 retrieved on Mar. 12, 2025 at https://www.echo-pilot.com/story/news/local/2022/09/01/coseytown-dollys-heart-is-dahlia-name-picked-at-old-home-week-greencastle-civil-war-gettysburg/65464333007/, 5 pp. (Year: 2022).*

Sullivan Facebook Valley Ridge Farm 2023 retrieved on Mar. 12, 2025 at https://www.facebook.com/groups/265949743891471/posts/1720992565053841/, 2 pp. (Year: 2023).*

Sweet Bloom Farm Karma Choc retrieved on Mar. 12, 2025 at https://www.sweetbloomfarm.com/products/karma-chocolate, 8 pp. (Year: 2025).*

* cited by examiner

*Primary Examiner* — June Hwu

(57) ABSTRACT

A new and distinct cultivar of *Dahlia* plant named 'LeeAnn's FD61A' is disclosed, characterized by a strong, upright growth habit, combined with free and early flowering. Flowers are held above the foliage canopy and have a consistent quality throughout the growing season. Flowering stems have an above average strength with a firm blossom attachment. Flower color is a deep magenta. Inflorescences have strong postproduction quality. The new variety is a *Dahlia* typically produced for cut flower purposes, or garden or landscape.

3 Drawing Sheets

Latin name of the genus and species: *Dahlia hybrida.*
Variety denomination: 'LeeAnn's FD61A'.

BACKGROUND OF THE INVENTION

The new *Dahlia* cultivar is a product of a planned breeding program conducted by the inventor, in Greencastle, Pennsylvania. The objective of the breeding program was to produce new *Dahlia* varieties with improved performance in open field conditions and produce cut flowers suitable for transport and sale. The open-pollination resulting in this new variety was made during 2018.

The seed parent is the unpatented, variety of *Dahlia* 'Fluffles'. The pollen parent is unidentified. Seed from 'Fluffles' was collected in 2018 and grown in a cultivated garden area in 2019. 'LeeAnn's FD61A' was intentionally selected from the seedlings that resulted based on the criteria of stem length and strength, upright growth habit, blossom attachment, petal count, and bloom color.

Asexual reproduction of the new cultivar was first performed by tubers by the inventor in Greencastle, Pennsylvania in the Spring of 2020 and has shown that the unique features of this cultivar are stable and reproduced true to type in successive generations.

SUMMARY OF THE INVENTION

The new cultivar 'LeeAnn's FD61A' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'LeeAnn's FD61A' These characteristics in combination distinguish 'LeeAnn's FD61A' as a new and distinct *Dahlia* cultivar:

1. Strong, upright growth habit.
2. Free branching.
3. Self-supporting plant habit.
4. Consistency of bloom quality throughout the growing season.
5. Early flowering.

6. Above average stem strength.
7. Firm blossom attachment.
8. Deep magenta flower color.

Plants of the new cultivar 'LeeAnn's FD61A' are similar to plants of the seed parent, in some horticultural characteristics, however, plants of the new cultivar 'LeeAnn's FD61A' differ in the following;

1. The new cultivar has a larger, deep magenta flower; 'Fluffles' has a lavender/pink flower with a cream center.

The pollen parent cannot be identified with certainty.

COMMERCIAL COMPARISONS

Plants of the new cultivar 'LeeAnn's FD61A' are comparable to the variety *Dahlia* 'Karma Choc', U.S. Plant Pat. No. 18,422. The two *Dahlia* cultivars are similar in most horticultural characteristics; however, the new cultivar 'LeeAnn's FD61A' differs in the following:

1. Flowers of the new cultivar are a decorative form; flowers of this comparator are waterlily form.
2. Flower color of the new variety is deep magenta; flower color of 'Karma Choc' is dark red in the center and medium red in the outer ray florets.
3. Plants of the new cultivar have more leaf coverage than plants of 'Karma Choc'.
4. Foliage of the new cultivar is lighter in color (137C) than foliage of 'Karma Choc', which has foliage colored 200A on the upper surface.

Plants of the new cultivar 'LeeAnn's FD61A' are comparable to the variety *Dahlia* 'LeeAnn's FD 47C', copending, application Ser. No. 18/999,407. The two *Dahlia* cultivars are similar in most horticultural characteristics; however, the new cultivar 'LeeAnn's FD61A' differs in the following:

1. Inflorescences of the new cultivar have on average 104 ray florets per arranged in 13 whorls; inflorescences of 'LeeAnn's FD47C' has on average 160 ray florets arranged in 11 whorls.

BRIEF DESCRIPTION OF THE PHOTOGRAPHS

The accompanying photograph in FIG. 1 illustrates in full color a typical flowering plant of 'LeeAnn's FD61A' grown outdoors, in the ground under cut flower production conditions. Age of the plant photographed is approximately 18 weeks from a tuber.

Figure 1:
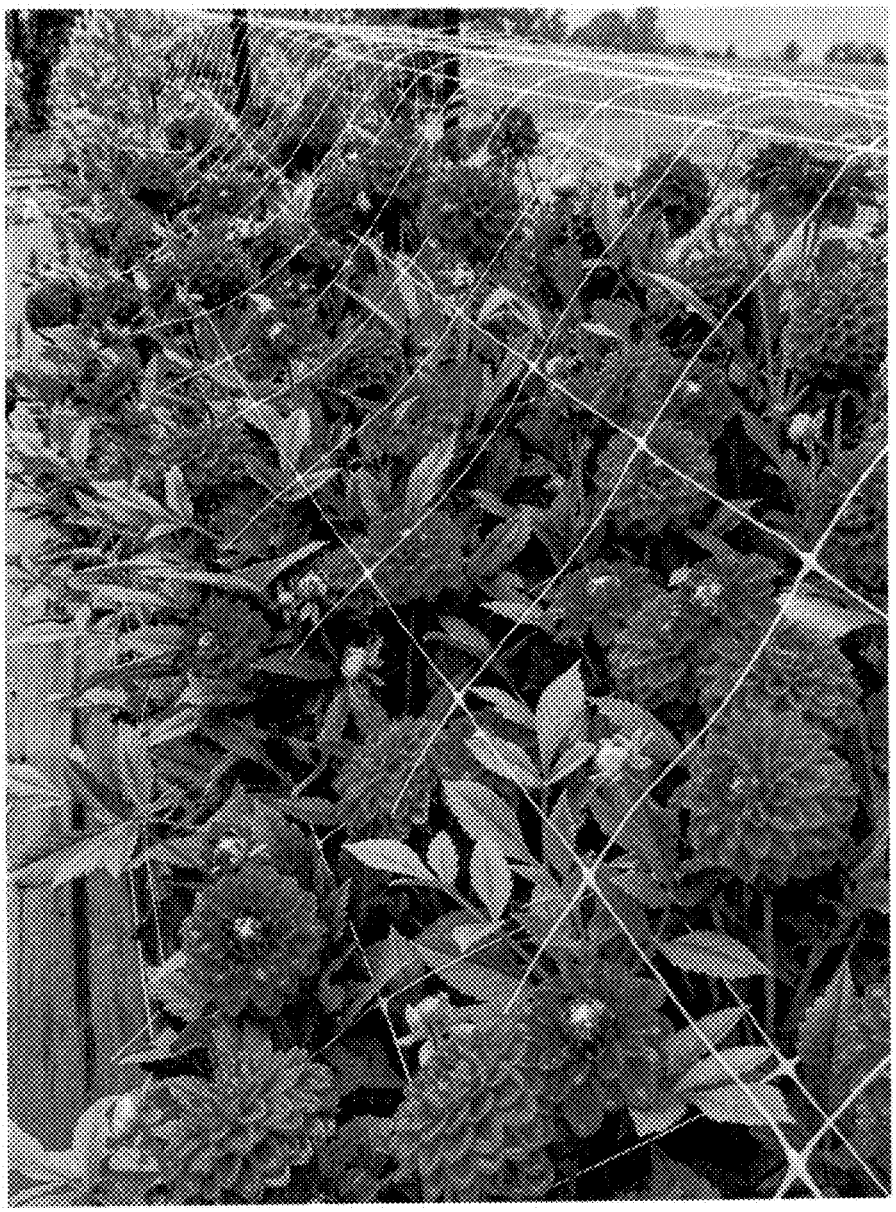
Figure 2:
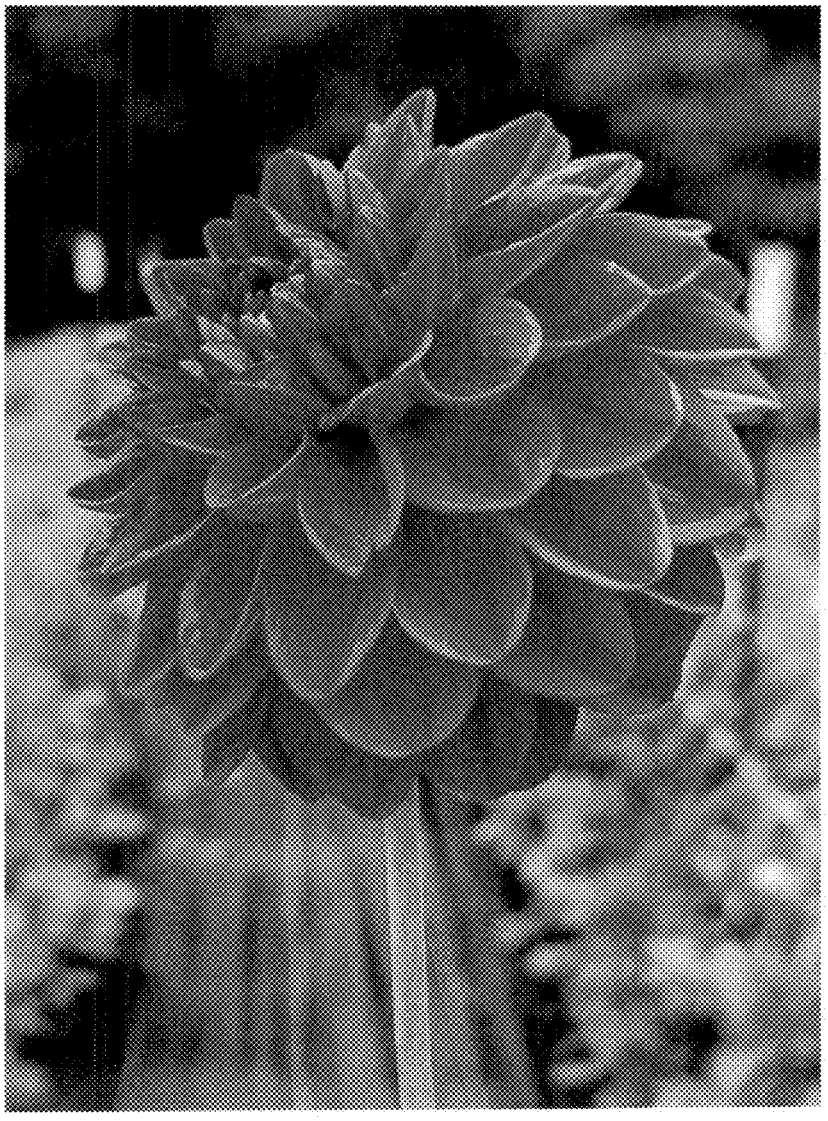
FIG. 2 illustrates a close-up of a typical flower.
Figure 3:
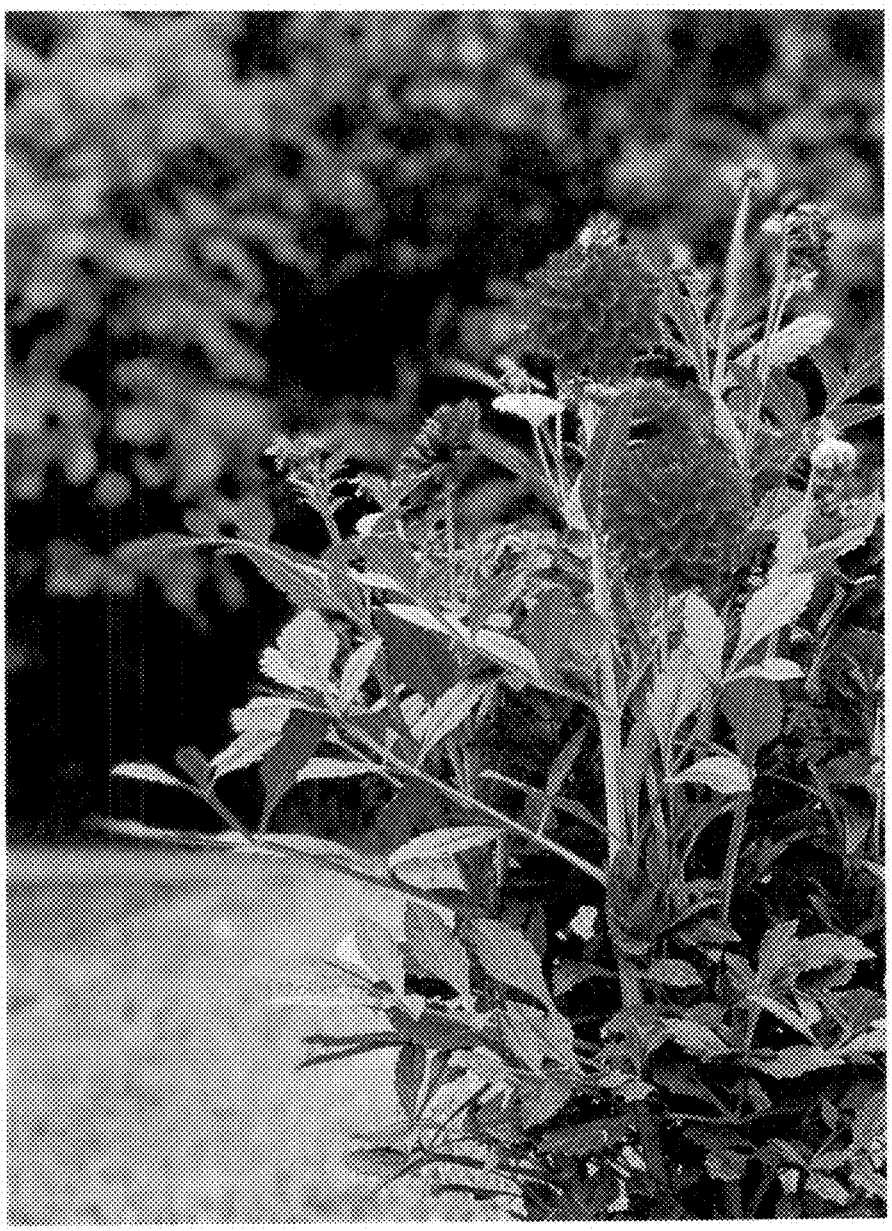
FIG. 3 is a plant of the new variety grown in a 3-gallon pot at about 9 months old.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society R.H.S. Colour Chart 2015 except where general terms of ordinary dictionary significance are used. The following observations and measurements describe 'LeeAnn's FD61A' plants grown outdoors in Greencastle, PA. The growing temperature ranged from about 5° C. to 30° C. during the day and from 3° C. to 10° C. during the night. General light conditions are bright, normal sunlight. Measurements and numerical values represent averages of typical plant types.

Botanical classification: *Dahlia hybrida* 'LeeAnn's FD61A'.

PROPAGATION

Type of propagation typically used: Vegetative terminal cuttings or tubers.

PLANT

Plant type: Herbaceous flowering perennial.

Growth habit: Strong, rounded growth habit that branches freely producing numerous strong stalks holding inflorescences at the leaf canopy. Vigorous growth and regrowth after continuous inflorescence harvesting. Plants are self-supporting and bloom earlier than the average *Dahlia* grown in the Inventor's test field.

Height: 108 cm.

Plant spread: 66 cm.

Growth rate: Vigorous.

Branching characteristics: Free-branching, lateral branches on average 40 cm long.

Lateral branch:

*Length.*—40 cm.

*Diameter towards base.*—13 mm.

*Diameter towards apex.*—13 mm.

*Angle of lateral branch from plant center.*—About 13.5°.

*Aspect.*—Erect to somewhat outwardly arching.

*Branch strength.*—Very strong, no flex or give.

*Texture.*—Smooth, glabrous with longitudinal sulcate grooves.

*Color.*—Upper and lower side, Green 143A.

FOLIAGE

Leaf:

*Shape.*—Ovate.

*Apex.*—Acute.

*Base.*—Oblique.

*Arrangement.*—Opposite. Single or composite with 3 to 7 leaflets.

*Length.*—Single leaves: About 94 mm. Compound leaves with three leaflets: About 120 mm. Compound leaves with five leaflets: About 144 mm. Compound leaves with seven leaflets: About 167 mm.

*Width.*—Single leaves: about 48 mm. Compound leaves with three leaflets: about 108 mm. Compound leaves with five leaflets: about 132 mm. Compound leaves with seven leaflets: About 144 mm.

*Attachment.*—Petiolate.

*Leaf wing.*—Absent to weak.

*Margin.*—Serrate.

*Texture of top surface.*—Glabrous.

*Texture of bottom surface.*—Glabrous.

*Color.*—Young foliage upper side: RHS Green 138A. Young foliage under side: RHS Green 138B. Mature foliage upper side: RHS Green 137C. Mature foliage under side: RHS Green 138B.

*Venation.*—Type: Pinnate. Venation color upper side: RHS Red 185A; midvein Green-Yellow 151C. Venation color under side: RHS Yellow-Green 150C.

Petiole:
*Single leaves.*—Length: 1.4 cm. Diameter: 30 mm.
*Compound leaves.*—Length: 30 to 34 mm. Diameter: 30 to 35 mm.
*Color.*—RHS Yellow-Green 144B.
*Texture.*—Glabrous all surfaces.

FLOWER

Time to flower: Plants begin to bloom around 72 days after planting, continuously blooming until season ending frost.
Inflorescence and flower type and habit: Fully double decorative *Dahlia* flower. Upright or slightly outwardly angled blossom position.
Position of Flower head in relation to foliage: Same level with foliage.
Post production longevity: Inflorescences maintain good substance on the plant for about 10 days and for about 5 days as a cut flower.
Fragrance: None.
Inflorescence size:
*Diameter.*—7.9 cm.
*Height.*—5 cm.
*Receptacle diameter.*—3.5 mm.
Bud:
*Shape.*—Oblate.
*Length.*—7.4 mm.
*Diameter.*—12 mm.
*Color.*—RHS Yellow-Green N144A.
*Texture.*—Glabrous.
Ray florets:
*Number of ray florets per inflorescence.*—About 104 arranged in 13 whorls.
*Density within inflorescence.*—Dense.
*Length.*—About 37 mm.
*Width.*—About 22.5 mm.
*Shape.*—Obovate.
*Apex.*—Obtuse.
*Base.*—Aequilateral.
*Aspect.*—Initially upright to slightly forward to the peduncle to cupped when completely reflexed.
*Profile in cross-section at mid-point.*—Strongly concave.
*Texture and appearance.*—Upper surface-Smooth, keeled, 2 keels, velvety with gold diamond dust reflective qualities. Lower surface-Smooth, velvety with gold diamond dust reflective qualities.
*Color.*—When opening, upper surface: Greyed-Purple 187B. When opening, lower surface: Main color Purple N79B and blended with vertical stripes White 155B. Fully opened, upper surface: Apex and margin Red-Purple 61A, mid-section and base Red 53A. Fully opened, lower surface-Red-Purple 72A blended into White 155B vertical stripes.
Disc florets:
*Number of disc florets per inflorescence.*—About 65.
*Shape.*—Tubular.
*Apex.*—Acute.
*Length.*—About 9 mm.
*Diameter, base.*—About 1 mm.
*Color.*—Apex yellow 9C, midsection N25C, base 2B.
Phyllaries:
*Quantity per inflorescence.*—Average 5 arranged in a single whorl.
*Length.*—About 13 mm.
*Width.*—About 5 mm.
*Shape.*—Oval.
*Apex.*—Acute.
*Base.*—Aequilateral.
*Margin.*—Entire.
*Texture.*—Upper and lower surfaces smooth, glabrous, waxy.
*Color.*—Upper Surface 137A, Lower Surface 137B.
Peduncle:
*Length.*—42 cm.
*Diameter.*—9 mm.
*Angle.*—Erect to about 14° from vertical.
*Strength.*—Exceptional with no bend or give.
*Texture.*—Glabrous, subtle sulcation.
*Color.*—RHS Yellow-Green 146C.

REPRODUCTIVE ORGANS

Disc florets:
Stamens:
*Number.*—5.
*Stamen attachment.*—Filament adnate to ventral surface of corolla.
*Stamen length.*—About 10 mm.
Anthers:
*Length.*—About 5 mm.
*Width.*—Less than 1 mm.
*Shape.*—Linear.
*Pollen.*—Quantity: Moderate. Color: Yellow-Orange 17A.
Pistil:
*Number.*—1.
*Length.*—About 17 mm.
*Stigma shape.*—Bifurcate.
*Stigma length.*—About 3 mm.
*Stigma width.*—About 0.4 mm.
*Stigma color.*—Yellow-Orange 17B.
*Ovary.*—Position: Inferior. Shape: Truncate. Length: 2 mm. Width: 1.3 mm. Color: RHS Green-White 157A.

OTHER CHARACTERISTICS

Fruit/seed: About 12 mm long, 2.5 mm wide, colored near Brown 200A.
Disease/pest resistance: Neither resistance nor susceptibility to has been observed.
Weather and climate performance: Plants of the new *Dahlia* have excellent tolerance to heat and high UV index, resisting wilting and fading in field grown conditions. Daylight length has minimal effects on bud and bloom production, maintaining cut flower output into late season light and weather conditions.
Temperature hardiness: Generally considered perennial in USDA zones 8-11. In USDA zones 6-7 the climate sometimes allows the tubers to be overwintered with proper protection. In USDA zones 5-3, considered an annual.

What is claimed is:

1. A new and distinct cultivar of *Dahlia* plant named 'LeeAnn's FD61A' as herein illustrated and described.

* * * * *